United States Patent
Kawamura et al.

(10) Patent No.: US 9,091,643 B2
(45) Date of Patent: Jul. 28, 2015

(54) DEVICE AND METHOD FOR ANALYZING KERNEL COMPONENT

(71) Applicants: Hiroshima University, Hiroshima (JP); Satake Corporation, Tokyo (JP)

(72) Inventors: Kensuke Kawamura, Hiroshima (JP); Hiroki Ishizuki, Tokyo (JP); Hideaki Ishizu, Tokyo (JP); Shinji Kaya, Tokyo (JP)

(73) Assignees: HIROSHIMA UNIVERSITY, Hiroshima (JP); SATAKE CORPORATION, Tokyo (JP)

( * ) Notice: Subject to any disclaimer, the term of this patent is extended or adjusted under 35 U.S.C. 154(b) by 294 days.

(21) Appl. No.: 13/655,591

(22) Filed: Oct. 19, 2012

(65) Prior Publication Data
US 2013/0278919 A1   Oct. 24, 2013

(30) Foreign Application Priority Data

Apr. 20, 2012 (JP) ................................ 2012-096945
Sep. 12, 2012 (JP) ................................ 2012-200893

(51) Int. Cl.
G01J 3/00 (2006.01)
G01N 21/3563 (2014.01)
G01J 3/28 (2006.01)
G01N 21/31 (2006.01)
G01N 21/359 (2014.01)
G01N 21/85 (2006.01)

(52) U.S. Cl.
CPC ........... *G01N 21/3563* (2013.01); *G01J 3/2823* (2013.01); *G01N 21/31* (2013.01); *G01N 21/359* (2013.01); *G01N 21/85* (2013.01); *G01J 2003/2873* (2013.01); *G01J 2003/2879* (2013.01)

(58) Field of Classification Search
CPC .................. G01J 2003/2873; G01J 2003/2879; G01J 2003/2823; G01J 3/42; G01N 21/31; G01N 21/3563; G01N 21/359; G01N 21/85
USPC ........................................................ 356/300
See application file for complete search history.

(56) References Cited

U.S. PATENT DOCUMENTS

2007/0016079 A1 *   1/2007   Freeman et al. .............. 600/476

FOREIGN PATENT DOCUMENTS

WO           WO 02/48687 A2      6/2002

OTHER PUBLICATIONS

Tachikawa, Tomoki, et al., "Estimation of Content Rate of Protein in Rice by Processing Infrared and Near-Infrared Spectral Images," Proceedings of the Japan Agricultural Systems Society, 2011 Autumn Meeting, Symposium and Research Presentation Summary of the Use of Biomass Resources and Activities by Local Districts for Creation of Low-Carbon Society, Oct. 22-23, 2011, 15 pages, System Agricultural vol. 27, Supplement 2, Japan.

*Primary Examiner* — Kara E Geisel
*Assistant Examiner* — Rufus Phillips
(74) *Attorney, Agent, or Firm* — Alston & Bird LLP

(57) ABSTRACT

A kernel component analysis device quantitatively analyzing a specific component contained in each of kernels on a kernel-by-kernel basis by spectroscopy includes: a light emitter configured to irradiate a kernel to be analyzed with light; a spectrum detector configured to detect a spectrum of light transmitted through and/or reflected from the kernel irradiated with the light; and a computing unit configured to calculate, on a kernel-by-kernel basis, a content of the specific component in the kernel to be analyzed, based on a spectrum value detected from an effective portion, which is suitable for quantitative analysis, of an image of the kernel by using a calibration curve indicating a relationship between a spectrum value at a specific wavelength and a content of the specific component.

14 Claims, 10 Drawing Sheets

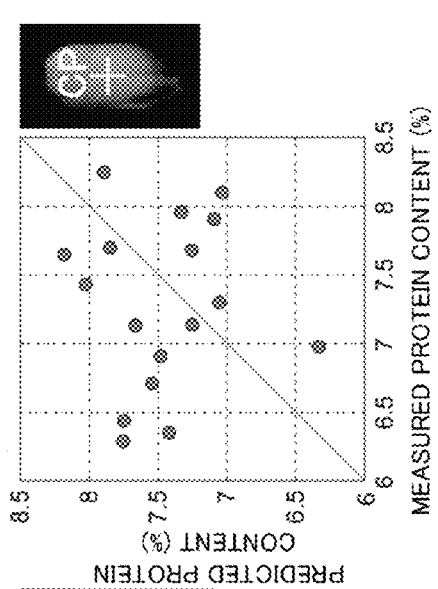
FIG.2A ENTIRE REGION(ER)
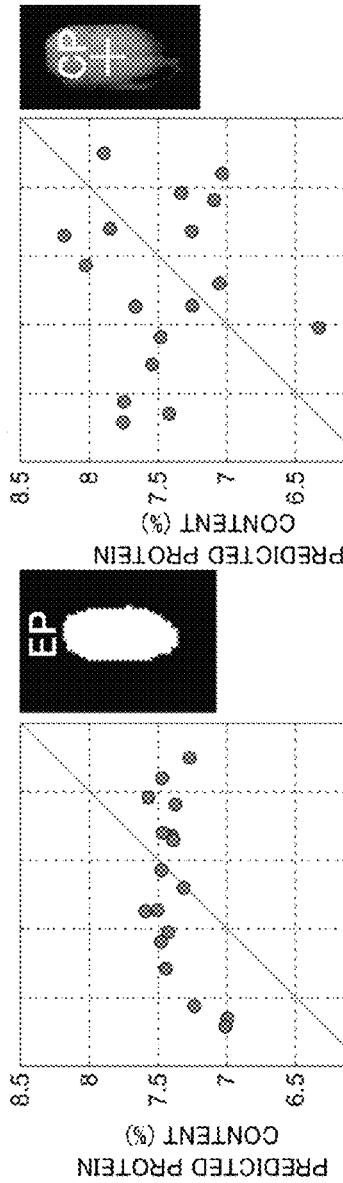
FIG.2B CENTRAL POINT(CP)
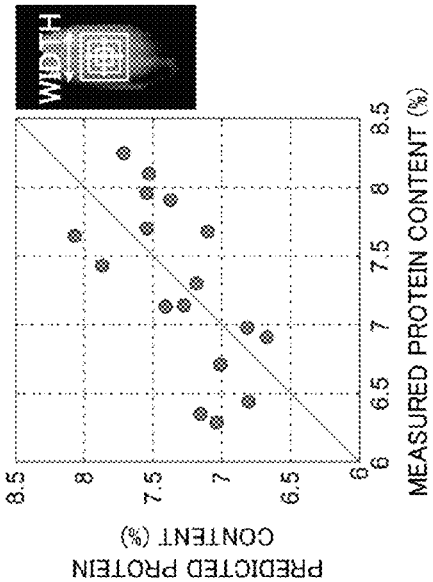
FIG.2C WEIGHTED CENTRAL POINT(WCP)
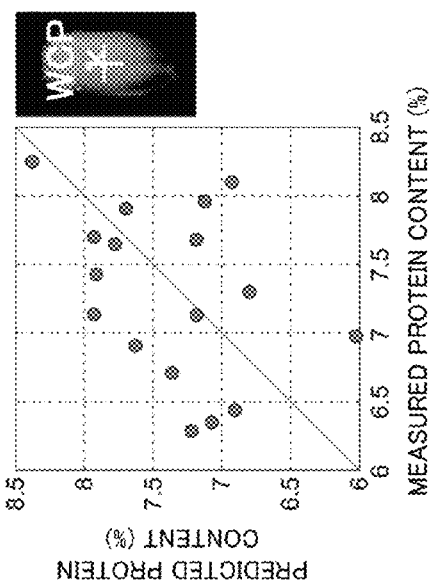
FIG.2D INSIDE OF BOX (WIDTH: 13 PIXELS)

DEVICE AND METHOD FOR ANALYZING KERNEL COMPONENT

CROSS-REFERENCE TO RELATED APPLICATIONS

This application claims priority to Japanese Patent Application No. 2012-096945 filed on Apr. 20, 2012, and Japanese Patent Application No. 2012-200893 filed on Sep. 12, 2012, the disclosure of each of which including the specification, the drawings, and the claims is hereby incorporated by reference in its entirety.

BACKGROUND

The present disclosure relates to devices and methods for analyzing kernel components, and more particularly relates to a device and method in which a specific component in a kernel is quantitatively analyzed in a real-time and nondestructive manner by spectroscopy.

The quality of rice which is example grain distributed in the market is evaluated by analyzing components, such as the granulating ratio, the opaque rice kernel content percentage, and the protein content percentage in brown rice. However, such quality evaluation is often performed by visual inspections or by crushing kernels, and thus, a new system enabling easy, rapid, and accurate evaluation of the grain quality currently needs to be developed.

In recent years, in the field of food products, near-infrared spectroscopy has been actively applied to component analysis in a laboratory; however, this analysis requires time to, for example, crush and pretreat a sample. In contrast, on the field scale, real-time and nondestructive examination technologies, such as paddy rice taste evaluation utilizing satellite images, and estimation of an ecosystem variable of paddy rice using vegetation indices, have been researched. Especially recent development of visible/near-infrared camera technologies and peripheral devices is enabling simpler measurement of spectral images at lower cost than before. A spectral image examination technology allowing non-contact and nondestructive examination of a target object is a technology which is very useful also for quality analysis and component analysis. For example, a technique has been known in which physical and scientific features of one or more seeds are analyzed in a real-time and nondestructive manner by near-infrared spectroscopy (see, e.g., International Patent Publication No. WO02/48687 A2).

Various researches on a component inspection technology utilizing near-infrared spectroscopy as described above have been advanced; however, a method which, when grain is analyzed on a kernel-by-kernel basis, provides sufficient measurement accuracy is not established.

Therefore, there is a need for a kernel component analysis device and method which, when kernel components are to be analyzed on a kernel-by-kernel basis, allow accurate measurement of the kernel components.

SUMMARY

In one aspect of the present disclosure, a kernel component analysis device quantitatively analyzes a specific component contained in each of kernels on a kernel-by-kernel basis by spectroscopy, and includes: a light emitter configured to irradiate a kernel to be analyzed with light; a spectrum detector configured to detect a spectrum of light transmitted through and/or reflected from the kernel irradiated with the light; and a computing unit configured to calculate, on a kernel-by-kernel basis, a content of the specific component in the kernel to be analyzed, based on a spectrum value detected from an effective portion, which is suitable for quantitative analysis, of an image of the kernel by using a calibration curve indicating a relationship between a spectrum value at a specific wavelength and a content of the specific component.

In another aspect of the present disclosure, a kernel component analysis method is directed to a kernel component analysis method in which a specific component contained in each of kernels is quantitatively analyzed on a kernel-by-kernel basis by spectroscopy, and includes: irradiating a kernel to be analyzed with light; detecting a spectrum of light transmitted through and/or reflected from the kernel irradiated with the light; and calculating, on a kernel-by-kernel basis, a content of the specific component in the kernel to be analyzed, based on a spectrum value detected from an effective portion, which is suitable for quantitative analysis, of an image of the kernel by using a calibration curve indicating a relationship between a spectrum value at a specific wavelength and a content of the specific component.

Generally, kernels each have a three-dimensional structure, and thus, the amount of light emitted from the light emitter and attenuated or reflected varies depending on the location through which the light is transmitted or the location from which the light is reflected. For example, the light transmitted through a central portion of a kernel is significantly attenuated, and the light transmitted through an outer portion of the kernel is insignificantly attenuated. Therefore, when the specific component contained in the kernel is calculated on a kernel-by-kernel basis based on the spectrum value detected from the effective portion, which is suitable for quantitative analysis, of the image of the kernel as in the device and method, the measurement accuracy can be improved.

The effective portion preferably has an area which is about 20-40% of an area of the image of the kernel.

In the device or method, the content of the specific component in the kernel may be calculated based on a spectrum value at a single wavelength or spectrum values at a plurality of discrete wavelengths. The light may be light in a near-infrared region, light in a visible region, or light from a visible region to a near-infrared region.

The device may further include: a carrier configured to carry kernels to a location at which each of the kernels is detected by the spectrum detector; and a screener configured to screen the kernels based on the corresponding contents of the specific component calculated by the computing unit. Thus, kernels fed into the device are carried, and can be each automatically screened depending on the content of the specific component in the corresponding kernel.

BRIEF DESCRIPTION OF THE DRAWINGS

The figures depict one or more implementations in accord with the present teachings, by way of example only, not by way of limitations. In the figures, like reference numerals refer to the same or similar elements.

FIGS. 2A-2D are various graphs illustrating the predicted protein content in each of rice kernels;

DETAILED DESCRIPTION

Embodiments are described in detail below with reference to the attached drawings. However, unnecessarily detailed description may be omitted. For example, detailed description of well known techniques or description of the substantially same elements may be omitted. Such omission is intended to prevent the following description from being unnecessarily redundant and to help those skilled in the art easily understand it.

Inventor provides the following description and the attached drawings to enable those skilled in the art to fully understand the present disclosure. Thus, the description and the drawings are not intended to limit the scope of the subject matter defined in the claims.

In the present disclosure, the term "kernel" is used herein to indicate a kernel of grain, and examples of grain include cereals, such as rice, barley, wheat, corn, millet, and Japanese barnyard millet, legumes, such as soya beans and adzuki beans, and pseudocereals, such as buckwheat. Examples of specific components include protein, starch, water, ash, and lipid. For the sake of convenience, a description is given by using rice kernels as example kernels, and using protein as an example specific component; however, the present disclosure is not limited to the following description.

(First Embodiment)

Figure 1:
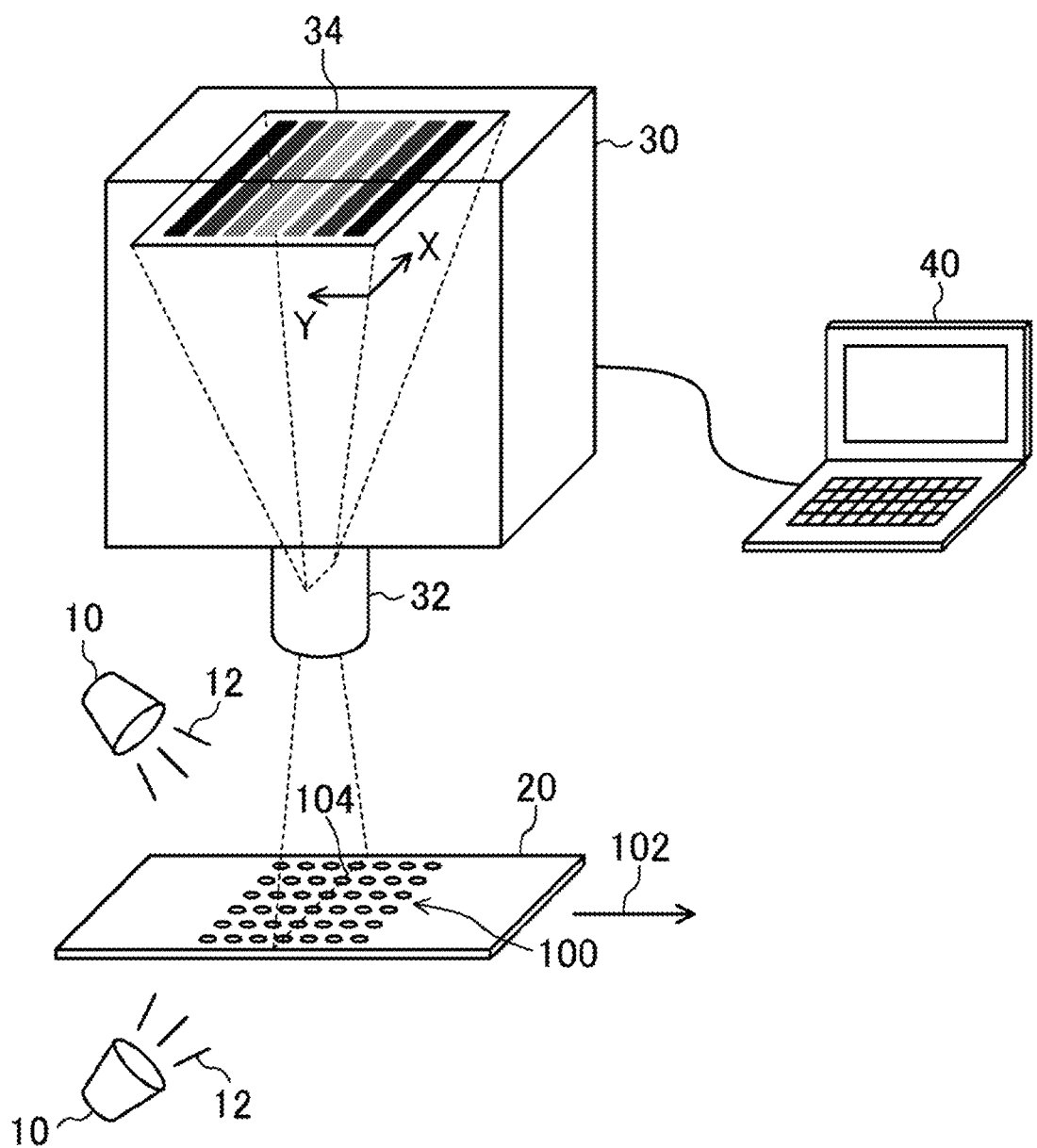
FIG. 1 is a schematic view illustrating a configuration of a kernel component analysis device according to a first embodiment.

FIG. 1 schematically illustrates a configuration of a kernel component analysis device according to a first embodiment. The kernel component analysis device according to this embodiment is configured to quantitatively analyze a specific component contained in a kernel by spectroscopy, and includes light emitters 10, a stage 20, a spectrum detector 30, and a computing unit 40.

The light emitters 10 are light sources from which light 12 in a near-infrared region in, e.g., the about 800-2500 nm wavelength range is emitted. For example, halogen lamps, xenon lamps, or LED lamps can be used as the light emitters 10. The light emitter 10 disposed below the stage 20 illuminates a plurality of kernels 100 arranged on the stage 20 at an angle of 45 degrees from below to supply transmitted light through the kernels 100 to the spectrum detector 30. In contrast, the light emitter 10 disposed above the stage 20 illuminates the kernels 100 arranged on the stage 20 at an angle of 45 degrees from above to supply reflected light from the kernels 100 to the spectrum detector 30.

Although, in this embodiment, the light emitters 10 are disposed both above and below the stage 20, either of the light emitters 10 may be omitted. Specifically, light for use in spectroscopy may be at least one of transmitted light through the kernels 100 or reflected light from the kernels 100. The illumination angle of the light 12 is arbitrary. Furthermore, the number of the light emitters 10 may be increased to irradiate the kernels 100 with light 12 from various angles.

The stage 20 moves in a direction of an arrow 102 with the kernels 100 placed thereon and being at rest. As described below, the spectrum detector 30 is configured to scan an image of the kernels 100 on a line-by-line basis, and the direction in which the stage 20 moves is a direction perpendicular to a scan line 104 when viewed in plan. An unshown stepper motor operates in synchronization with a shutter release of the spectrum detector 30 to move the stage 20. The stage 20 may be fixed, and the spectrum detector 30 may be moved.

The kernels 100 on the stage 20 may either be arranged in lines, or be arranged randomly. In order to more precisely measure the light transmitted through and/or reflected from each of the kernels 100, the kernels 100 are preferably prevented from being placed one on another. The kernels 100 may be arranged so as not to be placed one on another, for example, by forming a groove or recess in the surface of the stage 20. When the stage 20 is irradiated with the light 12 from below the stage 20, the stage 20 needs to be made of, e.g., acrylic resin or glass so as to be colorless and transparent.

The spectrum detector 30 can be achieved with a hyperspectral camera scanning an image of the kernels 100 arranged on the stage 20 on a scan-line-104-by-scan-line-104 basis, and simultaneously measuring the wavelength and spectrum value (e.g., a value indicating the transmittance of the wavelength) of each of pixels in a scan line 104. Specifically, light of a scan line 104 entering an optical system 32 including a lens and a spectroscope is dispersed with a predetermined wavelength resolution, the dispersed light is converted into an electric signal by a two-dimensional image sensor 34 comprised of, e.g., a complementary metal oxide semiconductor (CMOS) sensor or a charge-coupled device (CCD), and then, the electric signal is converted from analog to digital so as to be converted into a digit. In other words, spatial information and light dispersion information for the scan line 104 are detected as X-axis information and Y-axis information, respectively, of the two-dimensional image sensor 34. Then, the stage 20 is moved in synchronization with the obtainment of the information for the scan line 104 as described above, thereby obtaining a so-called spectral cube in which the spectral axis of each of pixels is added to a two-dimensional image of an object.

Since the light sensitivity of the spectrum detector 30 varies, a white reference plate and a black reference plate, for example, are preferably provided on the stage 20 to adjust maximum lightness (white) and minimum lightness (black) by imaging the reference plates before imaging a target object. The angle at which the spectrum detector 30 receives light is arbitrary.

The computing unit 40 calculates the content of a specific component in a kernel from the corresponding spectrum detected by the spectrum detector 30. The computing unit 40 can be achieved, for example, by allowing a computer to execute a computer program implementing a predetermined algorithm. The computing unit 40 and the spectrum detector 30 are connected together via wire or wireless communications.

Since the spectra of the individual kernels 100 of the same breed are detected, the content of a specific component contained in a kernel of the breed may be predicted based on, e.g., the average value of these spectra. Alternatively, after calculation of the contents of the specific component in the individual kernels 100, the average value of the calculated contents, for example, may be calculated to predict the content of the specific component contained in a kernel of the breed.

Generally, specific components contained in a material have different absorbances of light at a predetermined wavelength or in a predetermined wavelength range, and thus, the concentration, i.e., content, of a specific component contained in the material can be predicted based on absorbance. The computing unit 40 converts a spectrum value into, e.g., absorbance, and calculates the content of the specific component by using a calibration curve. Therefore, kernels of various breeds need to be chemically and spectrally analyzed in advance, and a calibration curve needs to be created by multivariate analysis, such as multiple regression analysis and partial least square (PLS) regression analysis, called chemometrics. The calibration curve may be retained in an unshown storage unit of the computing unit 40 so as to be read as appropriate, and may alternatively be downloaded from an unshown server computer via a network.

The computing unit 40 calculates the specific component contained in a kernel 100 by using the detected spectrum of, not an image of the entire kernel 100, but an image of a portion of the kernel 100 suitable for quantitative analysis (referred to as the "effective portion"). Various graphs in FIGS. 2A-2D each illustrate the predicted protein content in each of rice kernels. All of the graphs illustrate the predicted protein content in each of 17 breeds of rice kernels, in which the abscissa represents the content actually measured by chemical analysis, and the ordinate represents the content predicted by spectral analysis. A calibration curve is created by performing PLS regression analysis on the transmission spectrum of each of the breeds. One hundred rice kernels per breed are measured on a kernel-by-kernel basis.

FIG. 2A illustrates results each predicted using the spectrum of an entire rice kernel image. The planar shape of a typical rice kernel (short grain) is a generally oval shape having a length-to-width ratio of about 5:3. In this example, the lateral imaging resolution is about 20 pixels, the longitudinal imaging resolution is about 33 pixels, and the number of pixels in the entire rice kernel image is about 560 pixels. The planar shape of a rice kernel can be obtained by binarizing the corresponding spectrum. When the spectrum obtainment range the spectrum of which is to be obtained corresponds to an entire rice kernel image, the average spectrum of the pixels is used.

FIG. 2B illustrates results each predicted using the spectrum of a central point of a rice kernel image as the effective portion. The central point of the rice kernel image is the barycenter of the planar shape of the rice kernel obtained by the binarization.

FIG. 2C illustrates results each predicted using the spectrum of a weighted central point of a rice kernel image as the effective portion.

The weighted central point is the peak of the spectral distribution of the entire rice kernel image. In the present disclosure, the weighted central point is determined by a weighted average of the X and Y coordinates when the spectrum values of pixels of an image obtained by imaging a kernel are used as weights. Expressions are as follows:

Weighted Central Point $XW = \Sigma(i \cdot Pij)/\Sigma Pij$

Weighted Central Point $YW = \Sigma(j \cdot Pij)/\Sigma Pij$ where the characters i and j represent X and Y coordinate values, respectively, and the value Pij represent the spectrum value where (X, Y)=(i, j). The central point in the present disclosure is determined by arithmetic averaging.

FIG. 2D illustrates results each predicted using the spectrum of a generally central portion of a rice kernel image as the effective portion. The generally central portion in this example is a square region including 13 pixels in length and 13 pixels in width, and extending from the central point of the rice kernel image to the sixth pixel in four directions (left, right, up, down). When the spectrum obtainment range corresponds to the generally central portion of the rice kernel, the average spectrum of the pixels is used.

Table 1 illustrates various parameters indicating the correlation between the predicted values and the actually measured values in FIGS. 2A-2D. The value "R^2" (the square of R) in Table 1 denotes a coefficient of determination. The value "RMSE" denotes a root mean square error. The value "SEP" denotes the standard error (%) of prediction in calibration for a calibration curve. The value "RPD" denotes a criterion of the reliability of the prediction accuracy of the calibration curve, and is given by SD/SEP (where the value SD represent a standard deviation). The value "EI" denotes a performance index, and is given by 2×SEP/Range×100.

TABLE 1

| Spectrum Obtainment Range | R^2 | RMSE | SEP | RPD | EI |
|---|---|---|---|---|---|
| Entire Region | 0.165 | 0.622 | 0.595 | 1.087 | 54.085 |
| Central Point | 0.347 | 0.556 | 0.570 | 1.135 | 51.814 |
| Weighted Central Point | 0.476 | 0.557 | 0.529 | 1.223 | 48.069 |
| Box Width 1 (Area Ratio 0.18%) | 0.476 | 0.557 | 0.529 | 1.223 | 48.069 |
| Box Width 3 (Area Ratio 1.6%) | 0.544 | 0.432 | 0.444 | 1.457 | 40.358 |
| Box Width 5 (Area Ratio 4.5%) | 0.602 | 0.402 | 0.413 | 1.566 | 37.538 |
| Box Width 7 (Area Ratio 8.8%) | 0.600 | 0.401 | 0.411 | 1.575 | 37.335 |
| Box Width 9 (Area Ratio 14%) | 0.630 | 0.408 | 0.397 | 1.627 | 36.136 |
| Box Width 11 (Area Ratio 22%) | 0.649 | 0.404 | 0.388 | 1.668 | 35.249 |
| Box Width 13 (Area Ratio 30%) | 0.650 | 0.410 | 0.384 | 1.686 | 34.877 |
| Box Width 15 (Area Ratio 40%) | 0.626 | 0.429 | 0.396 | 1.635 | 35.955 |

As seen from FIGS. 2A-2D and Table 1, when the spectrum of the central point or weighted central point as the effective portion is used, the prediction accuracy is higher than when the spectrum of the entire rice kernel image is used. When the spectrum of the generally central portion as the effective portion is used, the prediction accuracy further increases. However, when the area of the generally central portion is too large, the prediction accuracy tends to decrease. Therefore, it is appropriate to use, as the generally central portion, a region of the rice kernel image having an area which is about 20-40% of the area of the rice kernel image.

As above, according to this embodiment, a specific component contained in a kernel can be measured in a nondestructive, non-contact, and real-time manner. Furthermore, kernel components are analyzed on a kernel-by-kernel basis, thereby determining the protein content or the percentage of the protein content on a kernel-by-kernel basis with higher accuracy than ever before.

The shape of the generally central portion as the effective portion is not limited to a square, and may be, e.g., a rectangle, a polygon, a circle, an oval figure, or a shape similar to the shape of the corresponding kernel. The weighted central point of the kernel image may be used as the central point of the generally central portion. The area (the number of pixels) of the effective portion (including the generally central portion) may be fixed such that the ratio of the area of the effective portion to the area of the entire kernel image is about an appropriate value. Alternatively, in contrast, the area of the effective portion may be appropriately changed with the area ratio fixed, depending on the area of the corresponding kernel image.

The location of the effective portion does not need to be limited to the vicinity of the kernel center, and an appropriate portion of a kernel image may be appropriately extracted from the kernel image. The shape of the effective portion is not limited, and may be, e.g., a polygon, a circle, an oval figure, or a shape similar to the shape of the corresponding kernel. Furthermore, two or more effective portions of the kernel image may be extracted from the kernel image, and, in addition, images of the effective portions do not always need to be in contact with one another.

The light 12 emitted by the light emitters 10 is not limited to near-infrared light, and may be light including a wavelength in the visible region.

Incidentally, spectral analysis does not always need to be performed using successive spectra in a wide wavelength range. Calibration curves of some of specific components to be analyzed can be created based on a spectrum value at a single wavelength or spectrum values at a plurality of discrete wavelengths.

Figure 3:
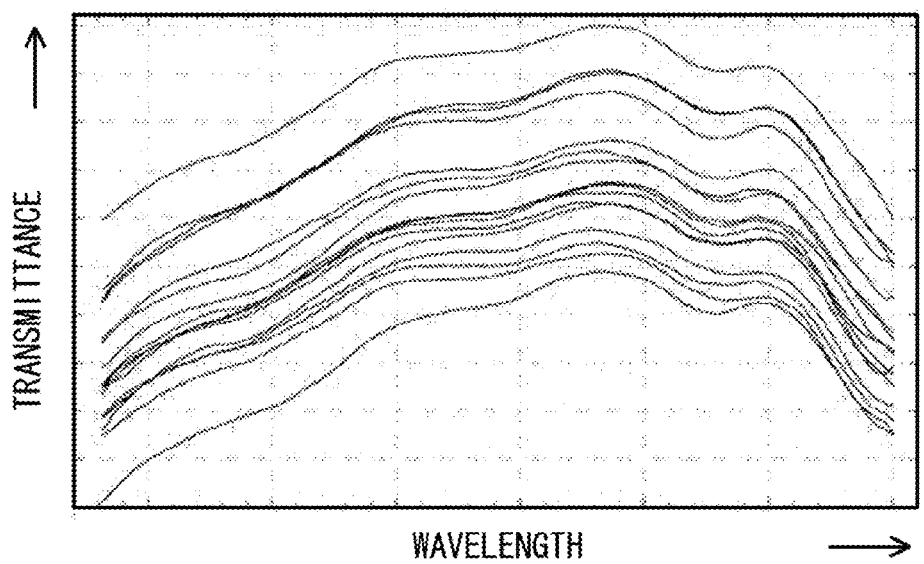
FIG. 3 is a graph illustrating the transmittances of light in a certain range of wavelengths from visible to near-infrared through 16 breeds of rice.

The graph in FIG. 3 illustrates the transmittances of light in a certain wavelength range from visible to near-infrared through 16 breeds of rice. In this example, the transmission spectra of all of the breeds each form an inverse V-shaped waveform having a peak in the vicinity of a certain wavelength.

Figure 4A:
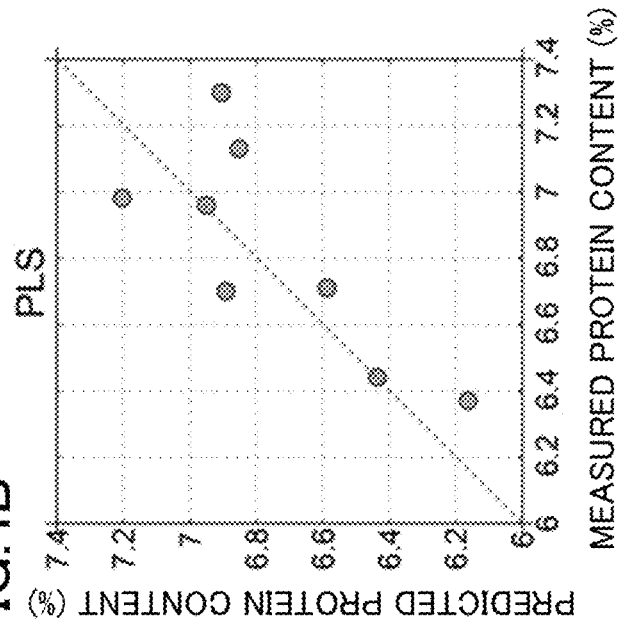
FIGS. 4A and 4B are various graphs illustrating the predicted protein content in each of rice kernels, which is obtained from the corresponding transmission spectrum in FIG. 3.
Figure 4B:
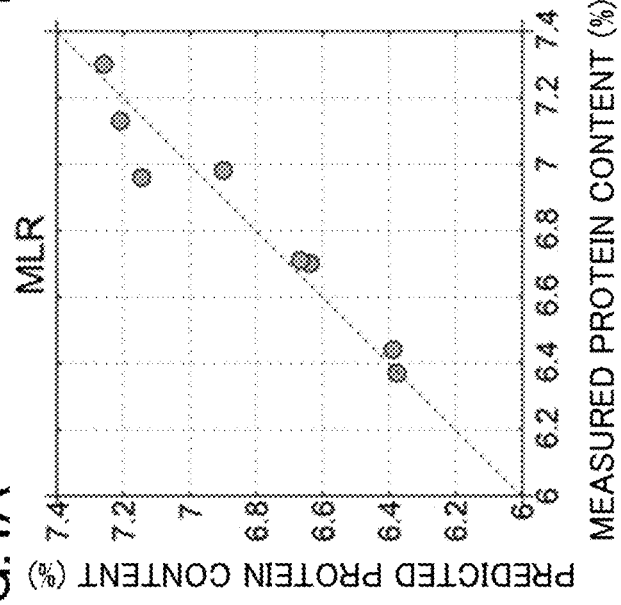

The various graphs in FIGS. 4A and 4B illustrate the predicted protein content in each of rice kernels, and the predicted protein content is obtained from the corresponding transmission spectrum in FIG. 3. The 16 breeds are classified into two groups; a calibration curve is created based on eight breeds in one of the two groups, and eight breeds in the other group are used to verify the calibration curve. The spectrum of a weighted central point of a rice kernel image is used as the spectrum of a corresponding rice kernel. FIG. 4A illustrates prediction results using a calibration curve created by multiple regression analysis. FIG. 4B illustrates prediction results using a calibration curve created by PLS regression analysis. In FIG. 4A, five discrete wavelengths are selected by forward stepwise selection, and multiple regression analysis is performed using the spectrum values at the wavelengths. While, in PLS regression analysis in FIG. 4B, the value $R^2$ is equal to 0.610, the value $R^2$ is equal to 0.939 in multiple regression analysis in FIG. 4A, and thus, in the multiple regression analysis, extremely accurate prediction results are provided.

When, as such, a calibration curve can be created based on a spectrum value at a single wavelength or spectrum values at a plurality of discrete wavelengths, not a hyperspectral camera, but an imager, such as a general area camera or a general line camera, can be used as the spectrum detector 30. This can provide a kernel component analysis device at low cost, and can also reduce the measurement time. An embodiment in which a hyperspectral camera is not used will be described hereinafter.

(Second Embodiment)

Figure 5:
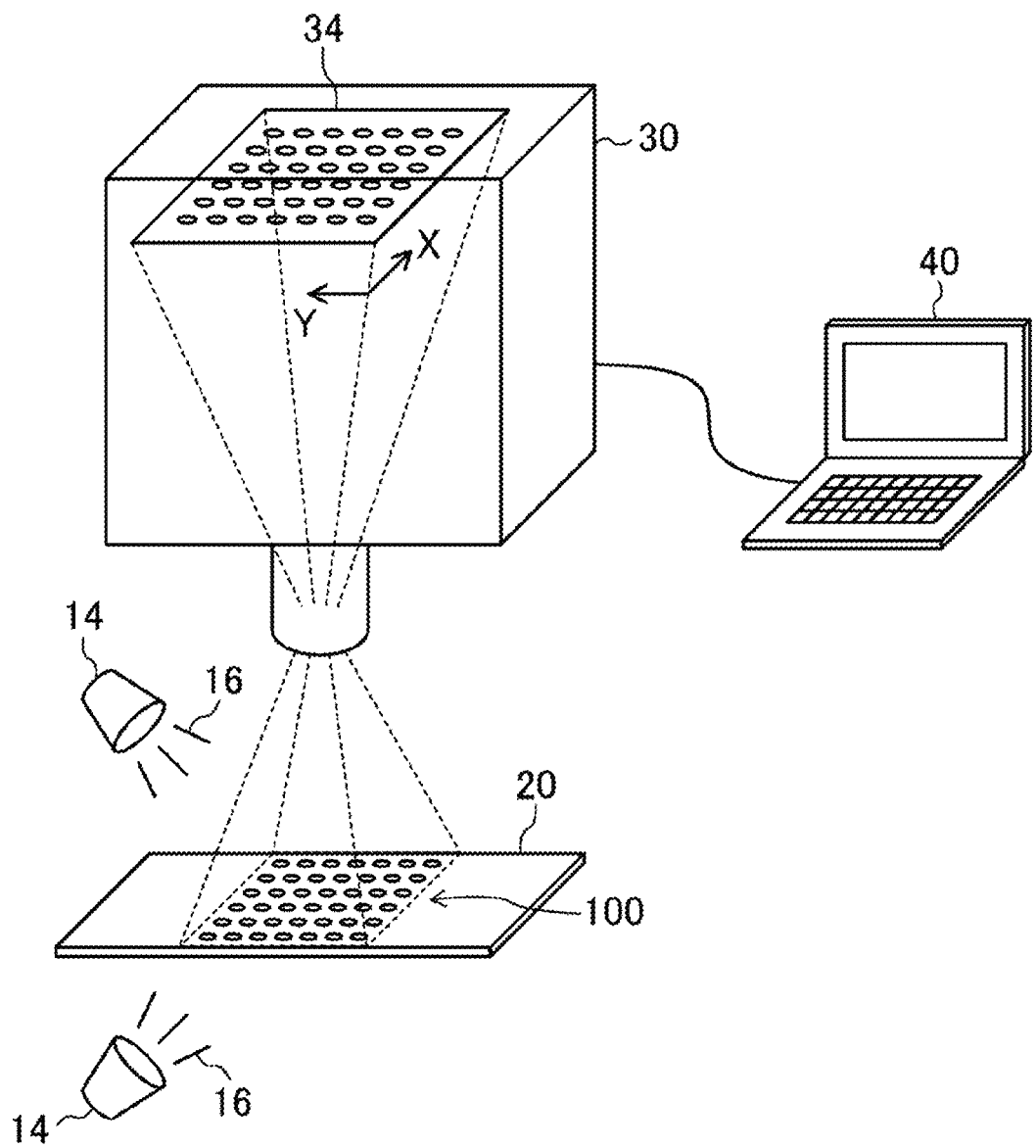
FIG. 5 is a schematic view illustrating a configuration of a kernel component analysis device according to a second embodiment.

FIG. 5 schematically illustrates a configuration of a kernel component analysis device according to a second embodiment. The kernel component analysis device according to this embodiment employs a so-called pre-spectroscopic system, in which kernels 100 on a stage 20 are irradiated with light at a predetermined wavelength, and a specific component in a kernel is quantitatively analyzed based on light transmitted through and/or reflected from the kernels 100. The following description is mainly given on aspects different from those in the first embodiment.

Light emitters 14 are light sources from which light 16 at a predetermined wavelength is emitted. The light emitters 14 can be each achieved, for example, by allowing the light emitter 10 of the kernel component analysis device according to the first embodiment to further include an optical filter through which light at the predetermined wavelength is transmitted. Furthermore, the kernels 100 on the stage 20 can be irradiated with light 16 at a plurality of discrete wavelengths by changing the pass band of the optical filter.

A spectrum detector 30 can be provided by an area camera configured to image, as a two-dimensional image, light transmitted through and/or reflected from the kernels 100 irradiated with light 16 at a specific wavelength. Specifically, the light transmitted through and/or reflected from the kernels 100 is converted into an electric signal by a two-dimensional image sensor 34 comprised of, e.g., a CMOS sensor or a CCD, and then, the electric signal is converted from analog to digital so as to be converted into a digit. In other words, light transmitted through or reflected from a two-dimensional region of the stage 20 is detected as X-axis information and Y-axis information of the two-dimensional image sensor 34. When the kernels 100 are to be imaged, the stage 20 or the spectrum detector 30 does not need to be moved.

(Third Embodiment)

Figure 6:
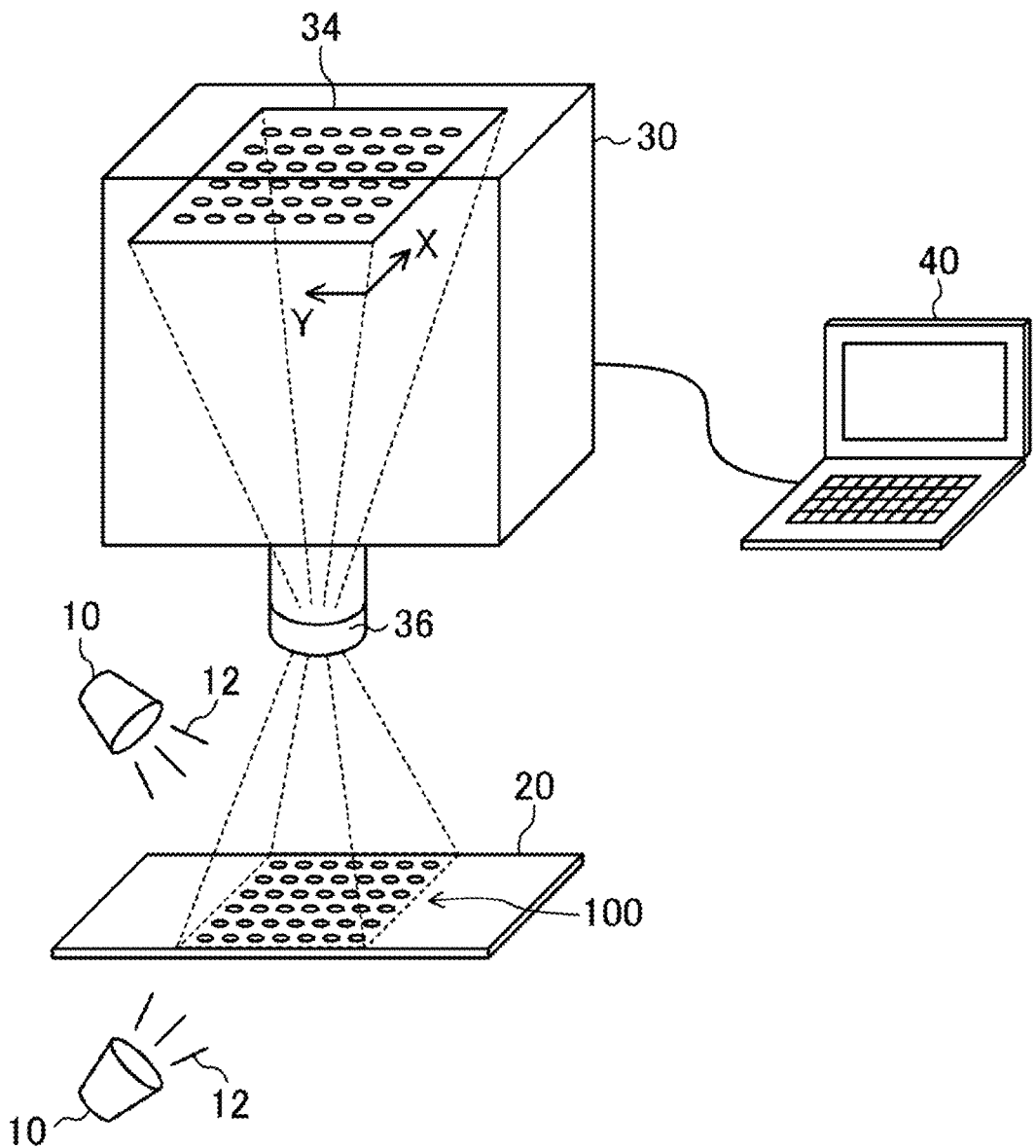
FIG. 6 is a schematic view illustrating a configuration of a kernel component analysis device according to a third embodiment.

FIG. 6 schematically illustrates a configuration of a kernel component analysis device according to a third embodiment. The kernel component analysis device according to this embodiment employs a so-called post-spectroscopic system, in which light at a predetermined wavelength of light transmitted through and/or reflected from kernels 100 on a stage 20 is filtered, and a specific component in a kernel is quantitatively analyzed based on the filtered light. The following description is mainly given on aspects different from those in the first embodiment.

A spectrum detector 30 can be provided by an area camera configured to image, as a two-dimensional image, light transmitted through and/or reflected from the kernels 100 on the stage 20. The spectrum detector 30 includes an optical filter 36 through which light at a predetermined wavelength is transmitted. The light at the predetermined wavelength in the light transmitted through and/or reflected from the kernels 100 is transmitted through the optical filter 36. The light filtered through the optical filter 36 is converted into an electric signal by a two-dimensional image sensor 34 comprised of, e.g., a CMOS sensor or a CCD, and then, the electric signal is converted from analog to digital so as to be converted into a digit. In other words, light transmitted through or reflected from a two-dimensional region of the stage 20 is detected as X-axis information and Y-axis information of the two-dimensional image sensor 34. When kernels 100 are to be imaged, the stage 20 or the spectrum detector 30 does not need to be moved.

Although, in the second and third embodiments, an area camera is used as the spectrum detector 30, a line camera may be used thereas. However, when a line camera is used, the stage 20 or the line camera itself is moved in synchronization with a shutter release of the line camera as in the first embodiment.

Kernels to be analyzed may be gravitationally dropped without providing the stage 20, and the gravitationally falling kernels may be imaged by a line camera.

(Fourth Embodiment)

Figure 7:
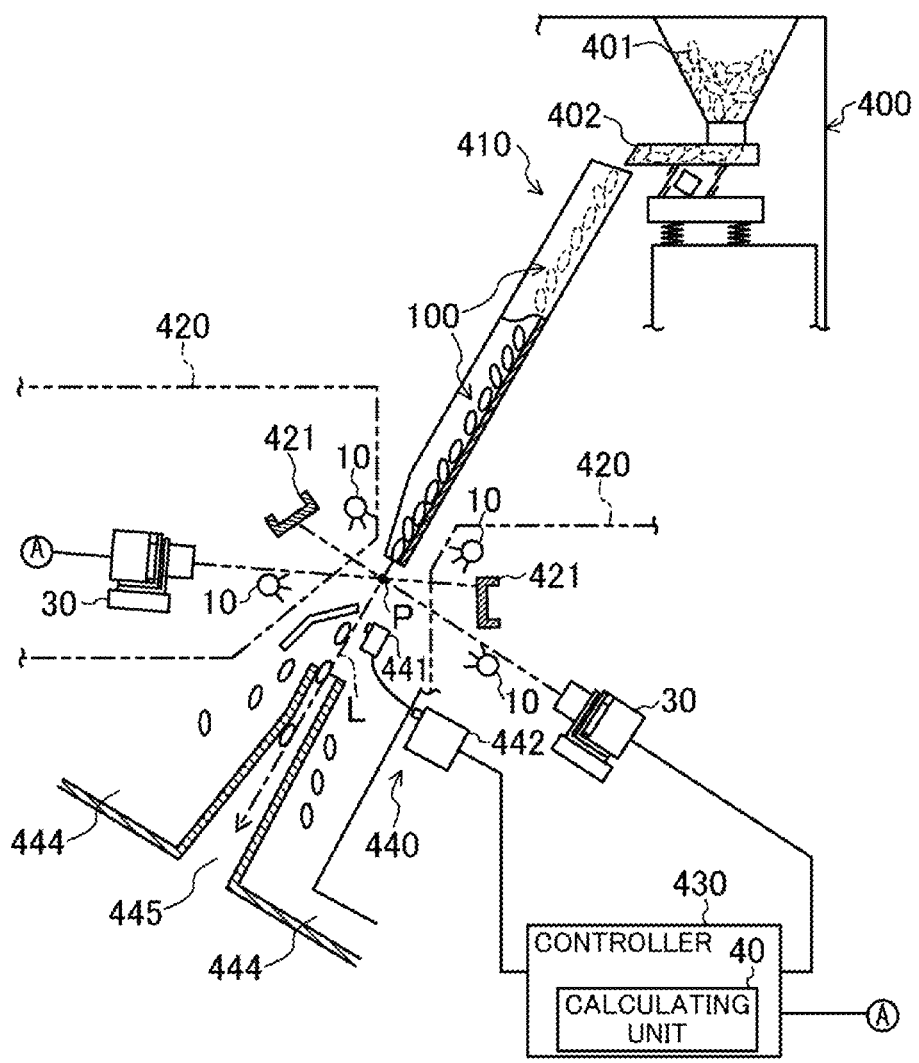
FIG. 7 is a longitudinal cross-sectional view of an essential portion of a kernel component analysis device according to a fourth embodiment.

FIG. 7 is a longitudinal cross-sectional view simply illustrating an essential portion and internal structure of a kernel component analysis device according to a fourth embodiment. The kernel component analysis device according to this embodiment includes a kernel feeder 400 including a tank 401 and a vibrating feeder 402 in an upper portion of the kernel component analysis device. Kernels 100 fed from the kernel feeder 400 gravitationally fall, in a successive manner, into a chute 410 with a predetermined width allowing the kernels 100 to fall while spreading laterally (successively fall while spreading laterally), and then, are released from the lower end of the chute 410 into the air along a fall path L through which the kernels 100 fall.

Two optical detectors 420 are arranged around the fall path L substantially symmetrically about the fall path L. The optical detectors 420 each include the above-described light emitters 10, the above-described spectrum detector 30, and a background plate 421. The light emitters 10 emit light at a predetermined wavelength from different angles to a detection location P at which the spectrum of a kernel 100 is detected and which is located on the fall path L. The spectrum detector 30 can be comprised of, e.g., a hyperspectral camera, an area camera, or a line camera, and images the kernels 100 which have reached the detection location P on the fall path L to detect the spectra of the kernels 100 on a kernel-by-kernel basis. The spectra detected by the spectrum detector 30 are sent to a controller 430. The controller 430 includes the above-described computing unit 40, and the computing unit 40 calculates the content of a specific component in each of the kernels 100 on a kernel-by-kernel basis.

The kernel component analysis device according to this embodiment further includes a screener 440 configured to screen the kernels 100 successively falling from the chute 410 while spreading laterally into good and defective kernels. The screener 440 includes an air nozzle 441 through which air is ejected to the fall path L, and an electromagnetic valve 442 configured to supply air to the air nozzle 441. Air is supplied from an unshown air compressor to the electromagnetic valve 442. When a kernel 100 having a content or content percentage of the specific component less than a predetermined value is detected, the controller 430 outputs a rejection signal to the electromagnetic valve 442 based on the analysis result of the computing unit 40. When receiving the rejection signal, the electromagnetic valve 442 opens an unshown valve, and air is ejected from the air nozzle 441, thereby blowing only defective kernels 100 off the fall path L with the ejected air. The blown defective kernels 100 are discharged through a defective kernel outlet 444 to the outside of the device. In contrast, good kernels 100 fall along the fall path L without being blown, and are discharged through a good kernel outlet 445 to the outside of the device.

(Fifth Embodiment)

Figure 8:
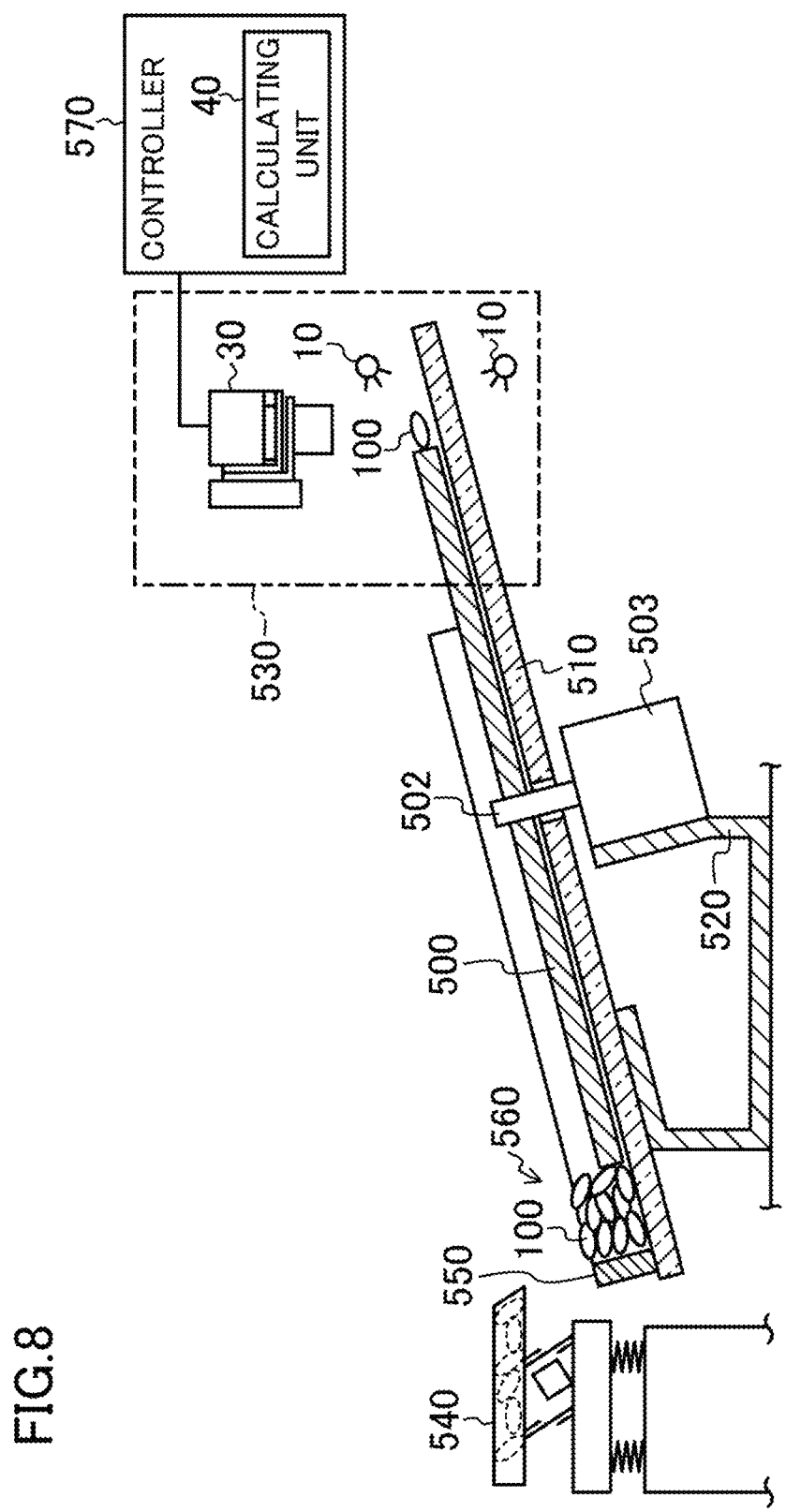
FIG. 8 is a longitudinal cross-sectional view of an essential portion of a kernel component analysis device according to a fifth embodiment.
Figure 9:
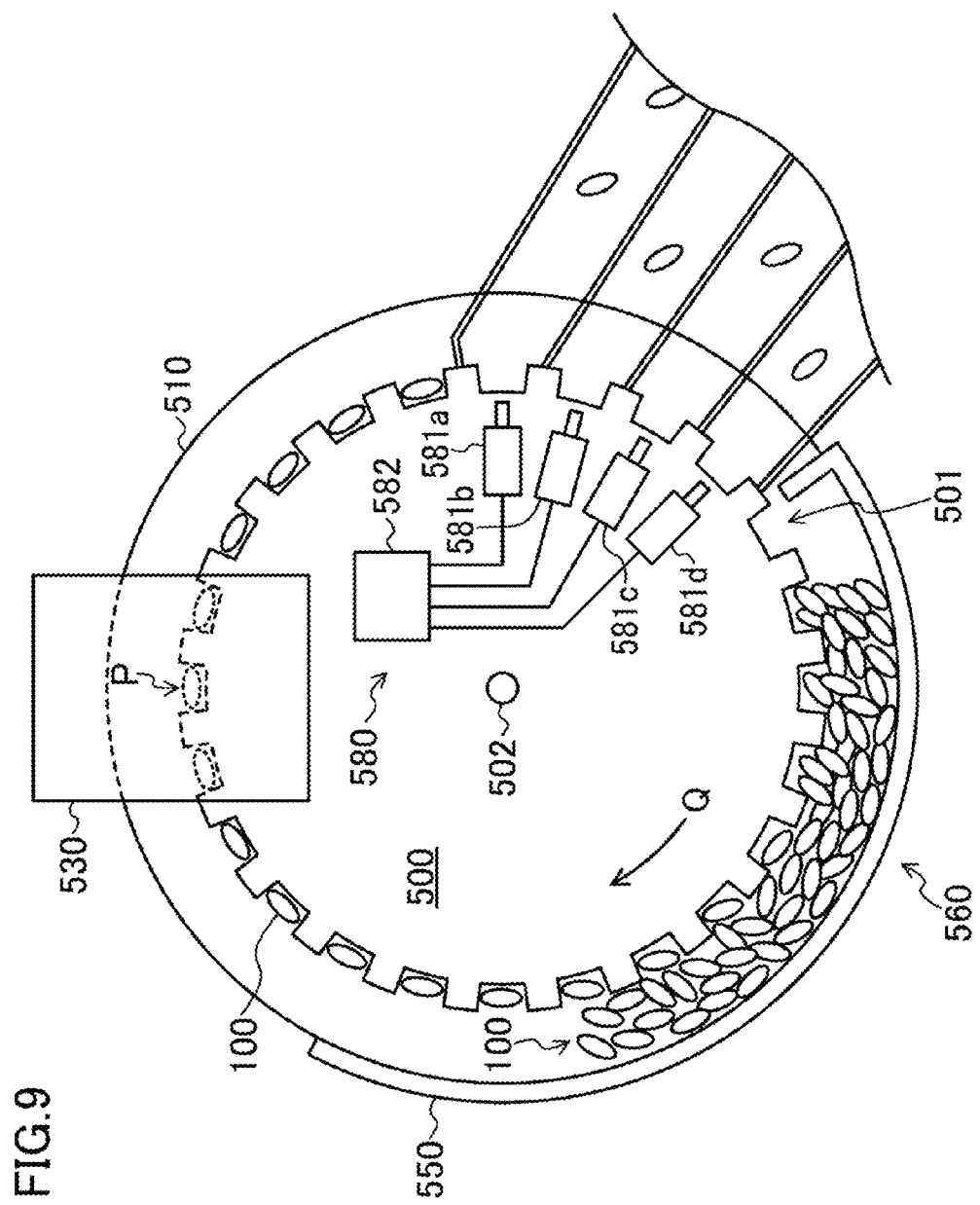
FIG. 9 is a plan view of an essential portion of the kernel component analysis device in FIG. 8.

FIG. 8 is a cross-sectional view simply illustrating an essential portion and internal structure of a kernel component analysis device according to a fifth embodiment. FIG. 9 is a plan view illustrating an essential portion of the kernel component analysis device. The kernel component analysis device according to this embodiment includes a disk 500. Recesses 501 in which kernels 100 can be placed are disposed in the perimeter of the disk 500, and the disk 500 rotates about a rotation shaft 502 in the direction of an arrow Q to carry the kernels 100. The disk 500 is placed on a transparent plate 510 having a larger diameter than the disk 500, and the rotation shaft 502 is rotationally driven by a drive motor 503 (speed reduction motor). The disk 500 and the transparent plate 510 are fixed to a base 520 together with the drive motor 503 while being inclined. An optical detector 530 is disposed near a portion of the circumferential surface of the inclined disk 500 facing upward, and a kernel feeder 540 is disposed near a portion of the circumferential surface of the inclined disk 500 facing downward. A partition 550 is provided to extend in the direction of rotation of the disk 500 from a portion of the circumferential surface of the transparent plate 510 facing downward, thereby forming a storage space 560 in which kernels 100 fed from the kernel feeder 540 can be stored.

The optical detector 530 includes the above-described light emitters 10, and the above-described spectrum detector 30. The light emitters 10 emit light at a predetermined wavelength from above and below a portion of the circumferential surface of the transparent plate 510 facing upward to a detection location P in a portion of the circumferential surface of the disk 500 facing upward. The spectrum detector 30 can be comprised of, e.g., a hyperspectral camera, an area camera, or a line camera, and images a kernel 100 which has reached the detection location P to detect the spectrum of the kernel 100. The spectrum detected by the spectrum detector 30 is sent to the controller 570. The controller 570 includes the above-described computing unit 40, and the computing unit 40 calculates the content of the specific component in the kernel 100.

The kernel component analysis device according to this embodiment further includes a screener 580 configured to screen kernels 100 carried by the disk 500. The screener 580 includes air nozzles 581a-581d each configured to eject air to a kernel 100 placed in a corresponding one of the recesses 501, and an electromagnetic valve 582 configured to supply air to the air nozzle 581a-581d. Air is supplied from an unshown air compressor to the electromagnetic valve 582. The controller 570 outputs a screening signal to the electromagnetic valve 582 based on the analysis result of the computing unit 40. When a target kernel 100 is carried to the location of a predetermined one of the air nozzles 581a-581d, the electromagnetic valve 582 opens an unshown valve in response to the screening signal, and air is ejected from the predetermined one of the air nozzles 581a-581d. Thus, the target kernel 100 on the transparent plate 510 is blown to the outside of the device with the ejected air; kernels 100 are thus screened based on corresponding component analysis results.

(Sixth Embodiment)

Figure 10:
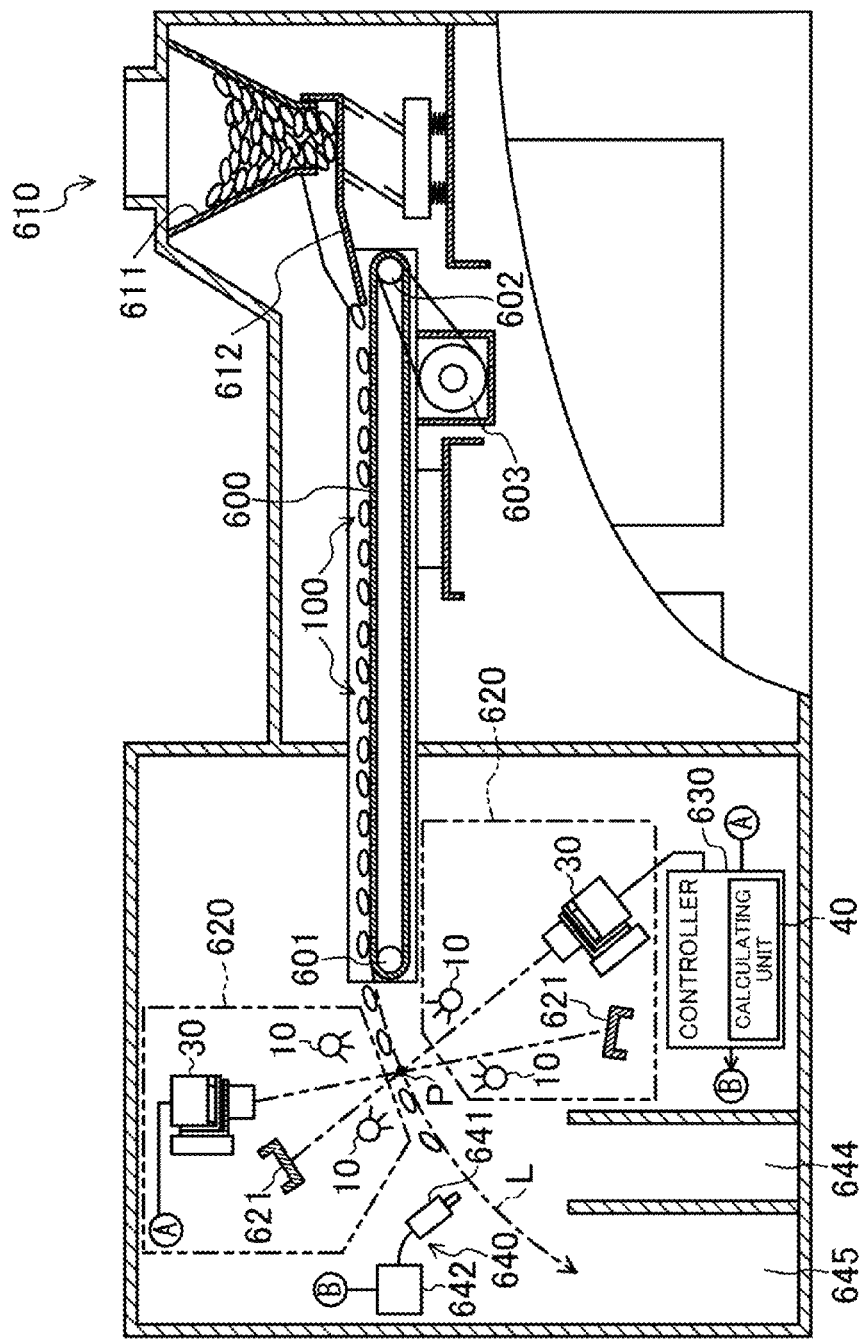
FIG. 10 is a longitudinal cross-sectional view of an essential portion of a kernel component analysis device according to a sixth embodiment.

FIG. 10 is a cross-sectional view simply illustrating an essential portion and internal structure of a kernel component analysis device according to a sixth embodiment. The kernel component analysis device according to this embodiment includes a carrying belt 600 configured to carry kernels 100, and a kernel feeder 610 configured to feed the kernels 100 to the carrying belt 600. The carrying belt 600 runs between rollers 601 and 602 arranged horizontally in parallel, and rotates at a fixed speed by a drive motor 603 coupled to the roller 602 through, e.g., a belt. The kernel feeder 610 includes a tank 611, and a vibrating feeder 612, and feeds kernels 100 to the beginning of the carrying belt 600. The kernels 100 fed from the kernel feeder 610 are released from the end of the carrying belt 600 into the air along a fall path L.

Two optical detectors 620 are arranged around the fall path L substantially symmetrically about the fall path L. The optical detectors 620 each include the above-described light emitters 10, the above-described spectrum detector 30, and a background plate 621. The light emitters 10 emit light at a predetermined wavelength from different angles to a detection location P on the fall path L. The spectrum detector 30 can be comprised of, e.g., a hyperspectral camera, an area camera, or a line camera, and images the kernels 100 which have reached the detection location P on the fall path L to detect the spectrum of the kernels 100 on a kernel-by-kernel basis. The spectrum detected by the spectrum detector 30 is sent to a controller 630. The controller 630 includes the above-described computing unit 40, and the computing unit 40 calculates the content of a specific component in each of the kernels 100 on a kernel-by-kernel basis.

The kernel component analysis device according to this embodiment further includes a screener 640 configured to screen, into good and defective kernels, kernels 100 released from the end of the carrying belt 600 into the air. The screener 640 includes an air nozzle 641 configured to eject air to the fall path L, and an electromagnetic valve 642 configured to supply air to the air nozzle 641. Air is supplied from an unshown air compressor to the electromagnetic valve 642. When a kernel 100 having a content or content percentage of the specific component less than a predetermined value is detected, the controller 630 outputs a rejection signal to the electromagnetic valve 642 based on the analysis result of the computing unit 40. When receiving the rejection signal, the electromagnetic valve 642 opens an unshown valve, and air is ejected from the air nozzle 641, thereby blowing only defective kernels 100 off the fall path L toward a defective kernel discharge chamber 644 with the ejected air. In contrast, good kernels 100 fall along the fall path L without being blown, and are contained in a good kernel discharge chamber 645.

In the fourth to sixth embodiments in each of which the kernel component analysis device includes a screener, kernels 100 can be not only screened into good and defective kernels but also classified into types for different uses. For example, when the kernels 100 are wheat kernels, the kernels 100 can be classified into kernels for pasta and kernels for bread, based on corresponding component analysis results. Furthermore, for example, when the kernels 100 are rice kernels, the kernels 100 can be classified depending on the percentages of the corresponding protein contents.

Other implementations are contemplated.

As described above, the first to sixth embodiments have been described as example techniques disclosed in the present application. However, the techniques according to the present disclosure are not limited to these embodiments, but are also applicable to those where modifications, substitutions, additions, and omissions are made. In addition, elements described in the first to sixth embodiments may be combined to provide a different embodiment.

Various embodiments have been described above as example techniques of the present disclosure, in which the attached drawings and detailed description are provided.

As such, elements illustrated in the attached drawings or the detailed description may include not only essential elements for solving the problem, but also non-essential elements for solving the problem in order to illustrate such techniques. Thus, the mere fact that those non-essential elements are shown in the attached drawings or the detailed description should not be interpreted as requiring that such elements be essential.

Since the embodiments described above are intended to illustrate the techniques in the present disclosure, it is intended by the following claims to claim any and all modifications, substitutions, additions, and omissions that fall within the proper scope of the claims appropriately interpreted in accordance with the doctrine of equivalents and other applicable judicial doctrines.

What is claimed is:

1. A kernel component analysis device quantitatively analyzing a specific component contained in each of kernels on a kernel-by-kernel basis by spectroscopy, comprising:
a light emitter configured to irradiate a kernel to be analyzed with light;
a spectrum detector configured to detect a spectrum of light transmitted through and/or reflected from the kernel irradiated with the light; and
a computing unit configured to calculate, on a kernel-by-kernel basis, a content of the specific component in the kernel to be analyzed, based on a spectrum value detected from a portion of an image of the kernel by using a calibration curve indicating a relationship between a spectrum value at a specific wavelength and a content of the specific component,
wherein:
said portion is a generally central portion of an endosperm of the kernel; and
an area of said portion is approximately 20-40% of an area of the image of the kernel.

2. The device of claim 1, wherein
the computing unit calculates the content of the specific component in the kernel, based on a spectrum value at a single wavelength or spectrum values at a plurality of discrete wavelengths.

3. The device of claim 1, wherein
the light emitter irradiates the kernel to be analyzed with light at the specific wavelength, and
the spectrum detector is an imager configured to image, as a two-dimensional image, the light transmitted through and/or reflected from the kernel irradiated with the light at the specific wavelength.

4. The device of claim 1, wherein
the spectrum detector is an imager configured to image, as a two-dimensional image, light at the specific wavelength in the light transmitted through and/or the reflected from the kernel.

5. The device of claim 1, wherein
the spectrum detector is a hyperspectral camera configured to scan an image of the kernel on a scan-line-by-scan-line basis, and simultaneously measure a wavelength and spectrum value of each of pixels for the scanned scan line.

6. The device of claim 1, wherein
the light is light in a near-infrared region.

7. The device of claim 1, wherein
the light is light in a visible region.

8. The device of claim 1, wherein
the light is light of any wavelength from a visible region to a near-infrared region.

9. The device of claim 1, further comprising:
a carrier configured to carry kernels to a location at which each of the kernels is detected by the spectrum detector; and
a screener configured to screen the kernels based on the corresponding contents of the specific component calculated by the computing unit.

10. A kernel component analysis method in which a specific component contained in each of kernels is quantitatively analyzed on a kernel-by-kernel basis by spectroscopy, the method comprising:
irradiating a kernel to be analyzed with light;
detecting a spectrum of light transmitted through and/or reflected from the kernel irradiated with the light; and
calculating, on a kernel-by-kernel basis, a content of the specific component in the kernel to be analyzed, based on a spectrum value detected from a portion of an image of the kernel by using a calibration curve indicating a relationship between a spectrum value at a specific wavelength and a content of the specific component,
wherein:
said portion is a generally central portion of an endosperm of the kernel; and
an area of said portion is approximately 20-40% of an area of the image of the kernel.

11. The method of claim 10, wherein
in the calculating of the content of the specific component, the content of the specific component in the kernel is calculated based on a spectrum value at a single wavelength or spectrum values at a plurality of discrete wavelengths.

12. The method of claim 10, wherein
the light is light in a near-infrared region.

13. The method of claim 10, wherein
the light is light in a visible region.

14. The method of claim 10, wherein
the light is light of any wavelength from a visible region to a near-infrared region.

* * * * *